(12) United States Patent
Babaev

(10) Patent No.: US 7,431,704 B2
(45) Date of Patent: Oct. 7, 2008

(54) APPARATUS AND METHOD FOR THE TREATMENT OF TISSUE WITH ULTRASOUND ENERGY BY DIRECT CONTACT

(75) Inventor: Eilaz Babaev, Minnetonka, MN (US)

(73) Assignee: Bacoustics, LLC, Minnetonka, MN (US)

( * ) Notice: Subject to any disclaimer, the term of this patent is extended or adjusted under 35 U.S.C. 154(b) by 0 days.

(21) Appl. No.: 11/449,220

(22) Filed: Jun. 7, 2006

(65) Prior Publication Data

US 2007/0287934 A1 Dec. 13, 2007

(51) Int. Cl.
*A61H 1/00* (2006.01)
*B05B 1/08* (2006.01)

(52) U.S. Cl. .................. 601/2; 239/102.2
(58) Field of Classification Search .............. 601/2–4; 606/169

See application file for complete search history.

(56) References Cited

U.S. PATENT DOCUMENTS

| | | | |
|---|---|---|---|
| 3,275,059 A | 9/1966 | McCullough | |
| 3,392,916 A | 7/1968 | Engstrom et al. | |
| 3,561,444 A | 2/1971 | Boucher | |
| 3,860,173 A | 1/1975 | Sata | |
| 4,052,004 A | 10/1977 | Martin et al. | |
| 4,085,893 A | 4/1978 | Durley, III | |
| 4,153,201 A | 5/1979 | Berger et al. | |
| 4,251,031 A | 2/1981 | Martin et al. | |
| 4,271,705 A | 6/1981 | Crostack | |
| 4,294,407 A | 10/1981 | Reichl et al. | |
| 4,301,093 A | 11/1981 | Eck | |
| 4,301,968 A | 11/1981 | Berger et al. | |
| 4,309,989 A | 1/1982 | Fahim | |
| 4,319,155 A | 3/1982 | Nakai et al. | |
| 4,334,531 A | 6/1982 | Reichl et al. | |
| 4,352,459 A | 10/1982 | Berger et al. | |
| 4,428,531 A | 1/1984 | Martin | |
| 4,466,571 A | 8/1984 | Muhlbauer | |
| 4,530,360 A | 7/1985 | Duarte | |
| 4,541,564 A | 9/1985 | Berger et al. | |
| 4,582,654 A | 4/1986 | Karnicky et al. | |

(Continued)

FOREIGN PATENT DOCUMENTS

WO 9717933 A1 5/1997

OTHER PUBLICATIONS

Babaev et al., First Experience of Using New Ultrasound Instrument for Treating Biological Tissue, article, 1973, pp. 57-59, 1st Ed. No. 165, Moscow Bauman School, Moscow, Russia.

(Continued)

*Primary Examiner*—Eric F Winakur
*Assistant Examiner*—Michael T Rozanski

(57) ABSTRACT

Apparatus and method for the treatment of tissue, such as hard and soft tissues, wounds, tumors, muscles, and cartilage, through the direct contact of ultrasound energy is disclosed. Ultrasound energy is delivered to a target area through direct contact with an ultrasound tip. Ultrasound energy is also delivered through direct contact with a coupling medium. The ultrasound tip is specially designed to comprise of a cavity area for controlled fragmentation and the simultaneous sonication of a target area. The specially designed ultrasound tip allows for ultrasound energy to focus on a target area. The ultrasound apparatus may be moved in a variety of different directions during the treatment of tissue.

11 Claims, 4 Drawing Sheets

U.S. PATENT DOCUMENTS

| | | | |
|---|---|---|---|
| 4,619,400 A | 10/1986 | Van Der Burgt |
| 4,642,581 A | 2/1987 | Erickson |
| 4,655,393 A | 4/1987 | Berger |
| 4,659,014 A | 4/1987 | Soth et al. |
| 4,679,551 A | 7/1987 | Anthony |
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,850,534 A | 7/1989 | Takahashi et al. |
| 4,877,989 A | 10/1989 | Drews et al. |
| 4,905,671 A | 3/1990 | Senge et al. |
| 4,930,700 A | 6/1990 | McKown |
| 4,941,618 A | 7/1990 | Hildebrand et al. |
| 4,961,885 A | 10/1990 | Avrahami et al. |
| 5,002,059 A | 3/1991 | Crowley et al. |
| 5,040,537 A | 8/1991 | Katakura |
| 5,063,922 A | 11/1991 | Hakkinen |
| 5,076,266 A | 12/1991 | Babaev |
| 5,104,042 A | 4/1992 | McKown |
| 5,115,805 A | 5/1992 | Bommannan et al. |
| 5,134,993 A | 8/1992 | van der Linden et al. |
| 5,163,433 A | 11/1992 | Kagawa et al. |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,231,975 A | 8/1993 | Bommannan et al. |
| 5,269,291 A | 12/1993 | Carter |
| 5,315,998 A | 5/1994 | Tachibana et al. |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief |
| 5,393,296 A | 2/1995 | Rattner |
| 5,431,663 A | 7/1995 | Carter |
| 5,437,606 A | 8/1995 | Tsukamoto |
| 5,474,071 A | 12/1995 | Chapelon et al. |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,526,815 A | 6/1996 | Granz et al. |
| 5,527,350 A | 6/1996 | Grove et al. |
| 5,529,572 A | 6/1996 | Spector |
| 5,545,124 A | 8/1996 | Krause et al. |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon |
| 5,616,140 A | 4/1997 | Prescott |
| 5,626,554 A | 5/1997 | Ryaby et al. |
| 5,643,179 A | 7/1997 | Fujimoto |
| 5,656,016 A | 8/1997 | Ogden |
| 5,658,323 A | 8/1997 | Miller |
| 5,699,805 A | 12/1997 | Seward et al. |
| 5,707,402 A | 1/1998 | Helm |
| 5,707,403 A | 1/1998 | Grove et al. |
| 5,720,287 A | 2/1998 | Chapelon et al. |
| 5,730,705 A | 3/1998 | Talish et al. |
| 5,735,811 A | 4/1998 | Brisken |
| 5,743,863 A | 4/1998 | Chapelon |
| 5,752,924 A | 5/1998 | Kaufman et al. |
| 5,762,616 A | 6/1998 | Talish |
| 5,785,972 A | 7/1998 | Tyler |
| 5,835,678 A | 11/1998 | Li et al. |
| 5,843,139 A | 12/1998 | Goedeke et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,895,362 A | 4/1999 | Elstrom et al. |
| 5,947,921 A | 9/1999 | Johnson et al. |
| 5,960,792 A | 10/1999 | Lloyd et al. |
| 5,989,245 A | 11/1999 | Prescott |
| 6,001,069 A | 12/1999 | Tachibana et al. |
| 6,007,499 A | 12/1999 | Martin et al. |
| 6,014,970 A | 1/2000 | Ivri et al. |
| 6,024,718 A | 2/2000 | Chen et al. |
| 6,026,808 A | 2/2000 | Armer et al. |
| 6,027,495 A | 2/2000 | Miller |
| 6,041,253 A | 3/2000 | Kost et al. |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,104,952 A | 8/2000 | Tu et al. |
| 6,106,547 A | 8/2000 | Huei-Jung |
| 6,113,558 A | 9/2000 | Rosenschein et al. |
| 6,113,570 A | 9/2000 | Siegel et al. |
| RE36,939 E | 10/2000 | Tachibana et al. |
| 6,158,431 A | 12/2000 | Poole |
| 6,176,839 B1 | 1/2001 | DeLuis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 | 6/2001 | Kollias et al. |
| 6,273,864 B1 | 8/2001 | Duarte et al. |
| 6,296,630 B1 | 10/2001 | Altman et al. |
| 6,314,318 B1 | 11/2001 | Petty |
| 6,321,109 B2 | 11/2001 | Ben-Haim et al. |
| 6,322,527 B1 | 11/2001 | Talish |
| 6,325,769 B1 | 12/2001 | Klopotek |
| 6,371,903 B1 | 4/2002 | Blanc et al. |
| 6,478,754 B1 | 11/2002 | Babaev |
| 6,533,803 B2 | 3/2003 | Babaev |
| 6,569,099 B1 | 5/2003 | Babaev |
| 6,601,581 B1 | 8/2003 | Babaev |
| 6,623,444 B2 | 9/2003 | Babaev |
| 6,663,554 B2 | 12/2003 | Babaev |
| 6,716,184 B2 | 4/2004 | Vaezy et al. |
| 6,723,064 B2 | 4/2004 | Babaev |
| 6,761,729 B2 * | 7/2004 | Babaev ................. 607/89 |
| 6,799,729 B1 | 10/2004 | Voic |
| 6,916,296 B2 | 7/2005 | Soring et al. |
| 7,025,735 B2 | 4/2006 | Soring et al. |
| 2006/0241470 A1 | 10/2006 | Novak et al. |
| 2006/0241533 A1 * | 10/2006 | Geller ................. 601/4 |

OTHER PUBLICATIONS

Isakov, U; Loshcilov, Kleimenov, V; Babaev, E., First Experience of Using New Ultrasound Instrument for Treating Biological Tissue. Ultrasound in Surgery, Proceedings of Moscow Bauman School. 1st Ed. No. 165. 1973. p. 57-59.

* cited by examiner

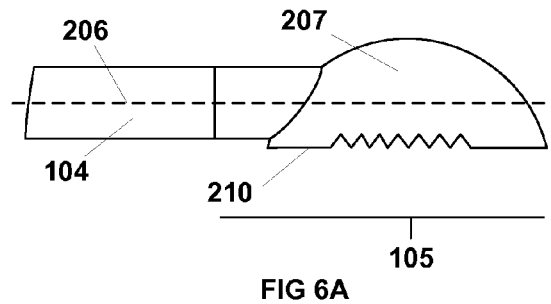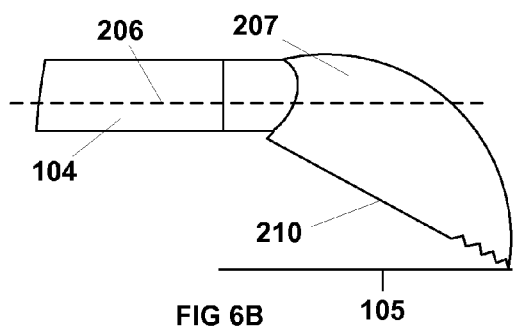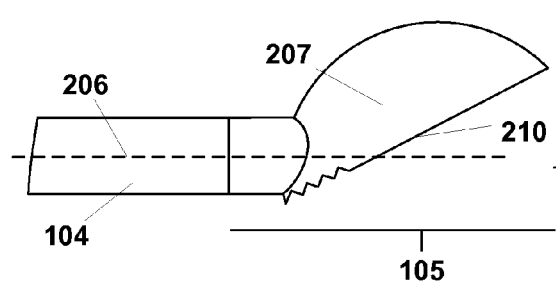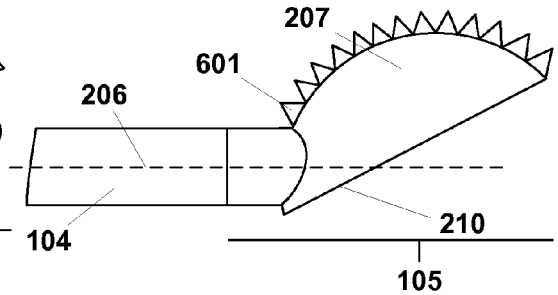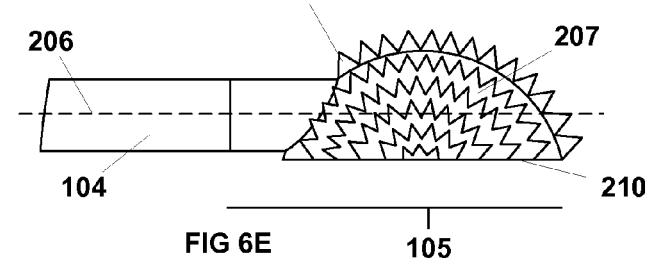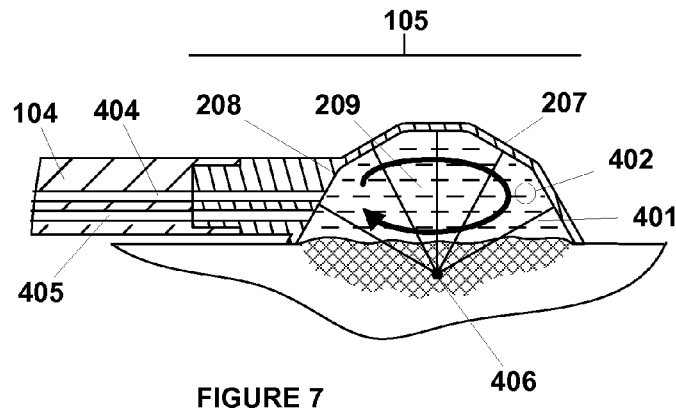

APPARATUS AND METHOD FOR THE TREATMENT OF TISSUE WITH ULTRASOUND ENERGY BY DIRECT CONTACT

BACKGROUND OF THE INVENTION

1. Field of the Invention

The present invention relates to apparatus and method for the treatment of tissue, such as hard and soft tissue, wounds, tumors, muscles, and cartilage, with ultrasound energy by direct contact.

2. Description of the Related Art

There are a variety of known methods for the treatment of tissue. These methods include wound dressings, hyperbaric oxygen treatment, growth factor therapy, antibiotics, surgery, physical therapy, vacuum therapy, electrical simulation, bioengineered tissue, ultraviolet light therapy, and tissue ultrasound. There are also a variety of known methods for the treatment of wounds with ultrasound energy.

U.S. patents that disclose devices and methods for wound treatment using an ultrasound spray include: U.S. Pat. No. 6,478,754 to Babaev; U.S. Pat. No. 6,761,729 to Babaev; U.S. Pat. No. 6,533,803 to Babaev; U.S. Pat. No. 6,569,099 to Babaev; U.S. Pat. No. 6,663,554 to Babaev; and finally U.S. Pat. No. 6,960,173 to Babaev. These devices and methods can only achieve limited results because there is no sufficient delivery of ultrasound energy to the target because there is no direct contract with the target area. U.S. Pat. Nos. 7,025,735 to Soring and 6,916,296 also to Soring disclose a method and device for the treatment of septic wounds that uses both a liquid aerosol and direct contact.

U.S. Patent Application 2004/0030254 to Babaev discloses a device and method for ultrasound wound debridement. Babaev discloses a device that causes debridement through mechanical vibration in the ultrasound tip. This device is also limited in that it uses only mechanical vibration for debridement.

Therefore, there is a need for a device and method that can use both mechanical vibration and ultrasound cavitation for fragmentation. There is also a need for a device and method that can simultaneously treat tissue and remove unwanted tissue through fragmentation.

SUMMARY OF THE INVENTION

The present invention is directed towards an apparatus and method for the treatment of tissue, such as hard and soft tissues, wounds, tumors, muscles, and cartilage, through the direct contact of ultrasound energy. Apparatus and methods in accordance with the present invention may meet the above-mentioned needs and also provide additional advantages and improvements that will be recognized by those skilled in the art upon review of the present disclosure.

The present invention comprises an ultrasound transducer and a specially designed ultrasound tip, for the treatment of tissue, connected to the transducer by an ultrasound horn. The specially designed tip allows for controlled fragmentation and simultaneous sonication of a treatment area, such as a wound and/or a tissue to be treated such as, bone, unwanted tissue layers, and infected tissues, via direct contact. The specially designed tip also focuses ultrasound energy onto a treatment area. The tip comprises a cavity formed by its radial sides. An example combination of an ultrasound horn and tip with a cavity area is one forming a shape similar to a spoon utensil. The opening of the cavity may be orientated parallel to the longitudinal axis of the ultrasound horn. Alternatively, the opening of the cavity may be orientated at an angle, with respect to the longitudinal axis of the horn. The edges and surfaces of the ultrasound tip may be smooth, rough/jagged, or any combination thereof. During treatment, a channel running at least partially through the horn before opening into the tip's cavity deliver a coupling medium into the cavity. The channel may also be used to extract fragmented tissue.

During treatment ultrasound energy is generally delivered to the tissue being treated from the radial side of the ultrasound tip. The ultrasound energy may be delivered directly by contacting the target areas with the ultrasound tip. The ultrasound energy may also be delivered indirectly by contacting the target area with the coupling medium delivered into the cavity. Any medium through which ultrasound energy is capable of traveling, except for a mist, aerosol spray, or atomized liquid, may be used as a coupling medium. Both the mechanical vibrations induced in the tip by the transducer and the cavitations induced within the coupling medium by the ultrasound energy traveling through the tip may fragment the tissue being treated. Tissue may also be treated by dragging the various portions of the vibrating tip across it.

BRIEF DESCRIPTION OF THE DRAWINGS

The present invention will be shown and described with reference to the drawings of preferred embodiments and clearly understood in detail. Like elements of the various embodiments depicted within the figures are equivalently numbered.

FIGS. 6A-E depict alternative embodiments of the ultrasound tip.

FIG. 7 is a cross-sectional view of an alternative embodiment of the ultrasound tip containing a polygonal cavity.

DETAILED DESCRIPTION OF THE INVENTION

The present invention is a method and device for the treatment of tissue through the direct contact of ultrasound energy. Preferred embodiments of the present invention in the context of an apparatus and methods are illustrated in the figures and described in detail below.

Figure 1:
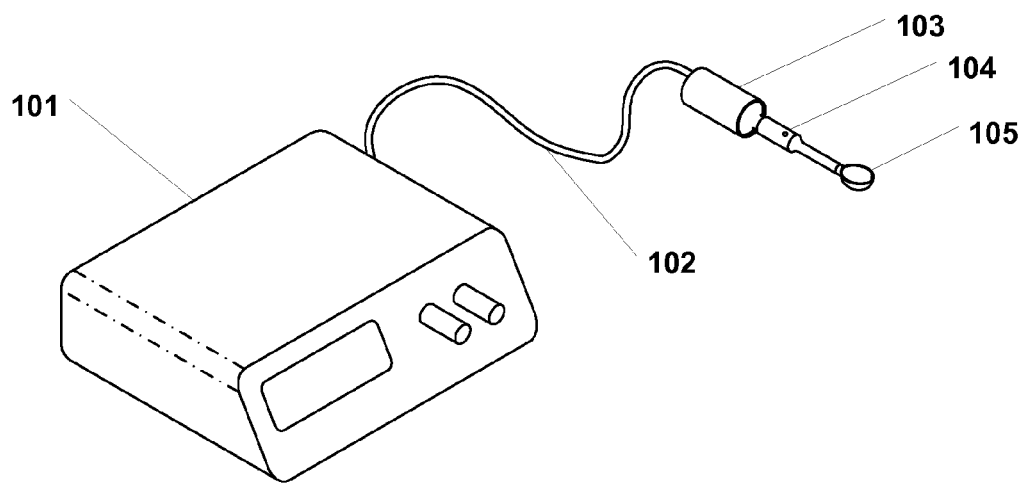
FIG. 1 is a perspective view of an ultrasound apparatus for the treatment of tissue according to the present invention.

FIG. 1 is a perspective view of an ultrasound apparatus for use according to the present invention that comprises an ultrasound generator 101, a power cable 102, an ultrasound transducer 103, an ultrasound horn 104, and a specially designed ultrasound tip 105. The ultrasound generator 101 may be battery powered or powered through an electrical outlet.

Figure 2:
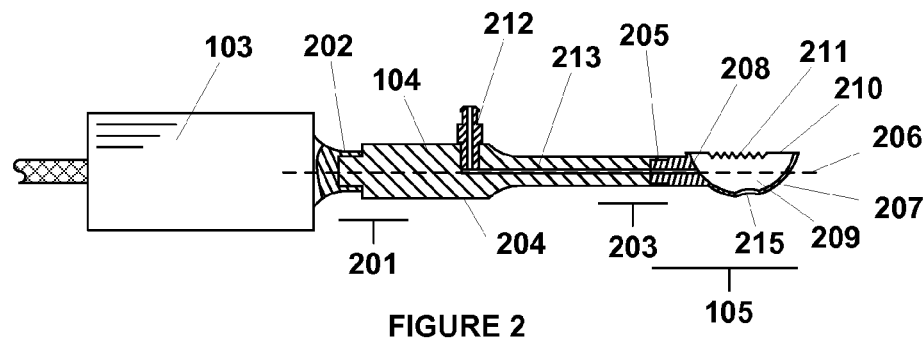
FIG. 2 is a cross-sectional view of the ultrasound apparatus for the treatment of tissue shown in FIG. 1.

FIG. 2 illustrates a cross-sectional view of the ultrasound apparatus for the treatment of tissue shown in FIG. 1. The ultrasound apparatus depicted in FIG. 2 comprises an ultrasound transducer 103 that is mechanically connected to the proximal end 201 of an ultrasound horn 104 by threading 202 or other means. Opposite the proximal end 201 of horn 104 is a distal end 203. Extending between the distal end 203 and the proximal end 201 of horn 104 is a radial surface 204. A longitudinal axis 206 extends through horn 104 from its proximal end 201 to its distal end 203. The distal end 203 of the ultrasound horn 104 is mechanically connected to an ultrasound tip 105 by threading 205 or other means. The preferred embodiment comprises an ultrasound transducer 103 that is connected to the ultrasound horn 104 by a mechanical interface; alternative embodiments could have the ultrasound transducer 103 directly connected to the ultrasound horn 104 to comprise a single piece without a mechanical interface. The preferred embodiment also comprises an ultrasound horn 104 that is connected to the ultrasound tip 105 by a mechanical interface; alternative embodiments could have the ultrasound 104 directly connected to the ultrasound tip 105 as to comprise a single piece without a mechanical interface. As can be seen in FIG. 2, the combination of the ultrasound horn 104 and tip 105 forms a shape similar to that of a spoon.

The tip 105 contains a back side 207. Opposite the back side 207 of tip 105 is a radial side 208 forming a parabaloid cavity 209 with an opening 210 orientated parallel to the longitudinal axis 206 of horn 104. At least partially encircling the opening 210 of cavity 209 is a jagged edge 211. Tip 105 may also contain an orifice 215 extending from its radial side 208 to its back side 207.

Channel 213, containing an opening within radial surface 204 of horn 104 and an opening within radial side 208 of tip 105, runs through at least a portion of horn 104 before opening into cavity 209. Channel 213 permits the delivery of a coupling medium to cavity 209.

Figure 3:
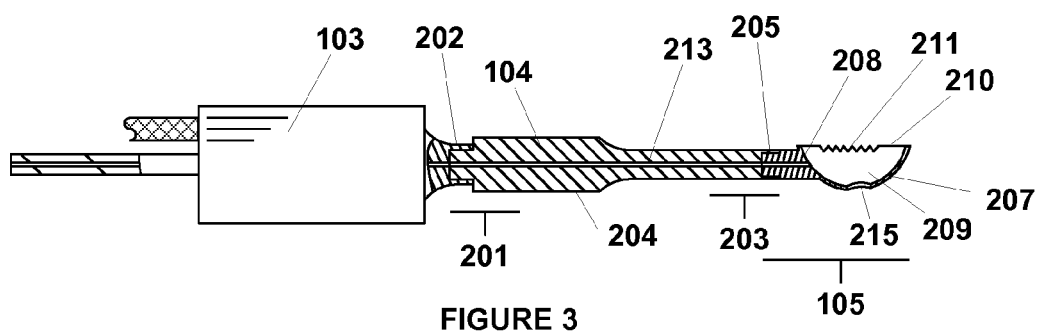
FIG. 3 is a cross-sectional view of an alternate embodiment of an ultrasound apparatus for the treatment of tissue.

FIG. 3 depicts a possible alternative embodiment of the ultrasound apparatus for the treatment of tissue. As illustrated in FIG. 3, channel 213 may also run through at least a portion transducer 103. In such an embodiment, channel 213 could be thought of two channels in communication with one another. The first channel would be a channel originating in a surface of transducer 103, other than its distal surface, and extending at least partially through transducer 103 before opening into the second channel. The second channel would be a channel originating within the proximal surface of horn 104 and running through horn 104 and into cavity 209.

The ultrasound apparatus for the treatment of tissue that depicted in FIG. 2 may further comprise an entry port 212 at the proximal end of channel 213. The entry port 212 may be orientated perpendicular to or at any other angle to axis 206 of the ultrasound horn 104. The preferred alignment for the entry port 212 is perpendicular to the ultrasound horn 104.

The ultrasound apparatus for the treatment of tissue may contain more than one channel extending at least partially through the horn, and possibly through the at least a portion of the transducer, before opening into the cavity of the tip. Including multiple channels opening into the cavity of the tip enables coupling medium to be extracted from the cavity and simultaneously delivered to the cavity in order to continually supply the cavity with fresh coupling medium. When multiple channels are used, the channel delivering coupling medium to the cavity may be smaller than the channel through which the coupling medium is extracted. Fragmented tissue may also be extracted along with the coupling medium. The preferred embodiment of an ultrasound apparatus for the treatment of tissue comprises a channel running through the transducer and the horn before opening into the cavity of the tip, utilized to delivery coupling medium to the cavity, and a channel originating in a radial surface of the horn and extending partially through the horn before opening into the cavity of the tip, that is utilized for extracting coupling medium from the cavity. If two channels originating in radial surfaces of the horn and extending partially through the horn before opening into the cavity of the tip are utilized, it is preferred that each channel originates on a opposite side of the ultrasound horn.

Figure 4:
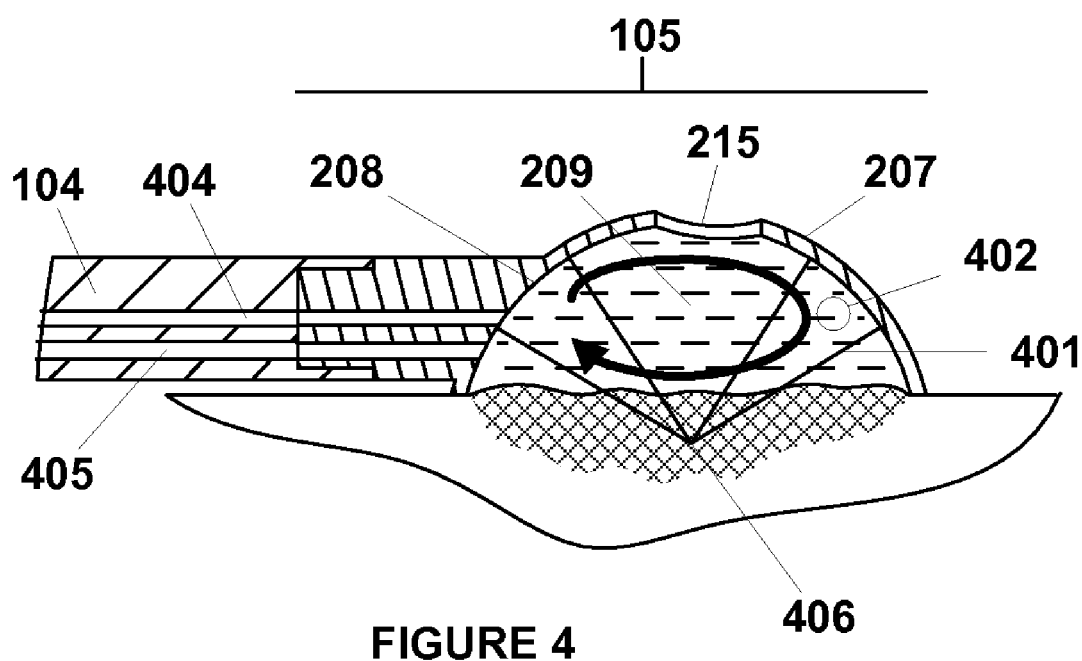
FIG. 4 is a detailed cross-sectional schematic representation of the delivery of ultrasound energy.

FIG. 4 details the delivery of ultrasound energy 401 from the radial side 208 of tip 105, through a coupling medium 402. The specific embodiment depicted comprises a delivery channel 404 for delivering coupling medium 402 into cavity 209 and an extraction channel 405 for extracting coupling medium 402 from cavity 209. Forming a paraboloid cavity 209, the radial side 208 focuses the ultrasound energy 401 emanating from the tip 105 towards focus 406 of the paraboloid cavity 209. Focus 406 of the paraboloid cavity 209 need not lay outside cavity 209, as depicted in FIG. 4. It may be beneficial to simultaneously deliver and extract coupling medium 402 from cavity 209. When simultaneously delivered and extracted from cavity 209, coupling medium 402 would enter cavity 209 from channel 404 and then strike the radial side 208 and circle back around before exiting cavity 209 through channel 405, possibly creating a vortex motion.

Figure 5A:
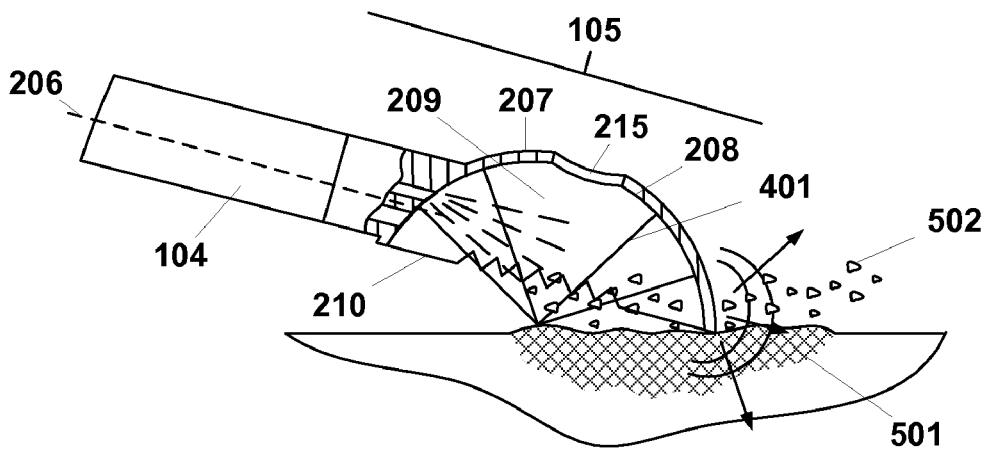
FIGS. 5A-C depict an example tissue treatment method using an embodiment of the ultrasound apparatus for the treatment of tissue.
Figure 5B:
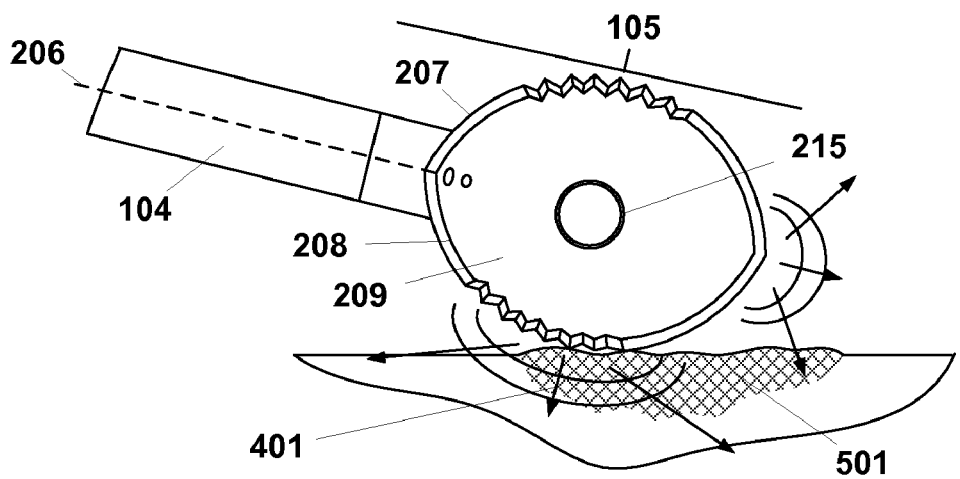
Figure 5C:
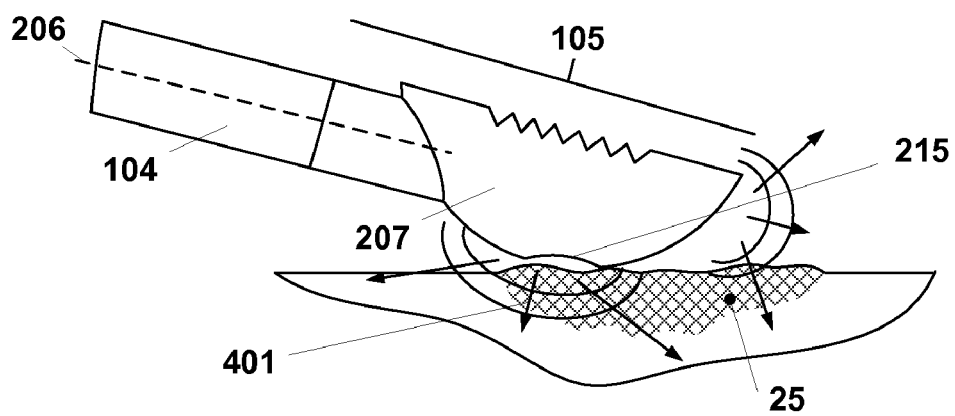

FIGS. 5A-C illustrate a possible method of using an embodiment of the ultrasound apparatus to treat tissue. As depicted in FIG. 5A, an edge adjacent to opening 210 of the cavity 209 formed by the radial side 208 of tip 105 is dragged across the tissue 501 to be treated. As an edge adjacent to opening 210 is dragged across tissue 501, tip 105 is ultrasonically vibrated. The mechanical motion of the vibration of tip 105 fragments unwanted tissue 502 from the tissue 501 being treated. If a coupling medium is simultaneously delivered to cavity 209, the fragmentation of tissue 501 may be enhanced by cavitations created within the coupling medium. In addition to possible enhancing fragmentation, delivering a coupling medium to cavity 209 may enhance the transmission of ultrasonic energy 401 from the radial side 208 to tissue 501. Holding tip 105 at an angle, as depicted in FIG. 5A, permits the ultrasonic energy 401 emanating from radial 208 to be focused onto tissue 501.

Back side 207 of tip 105 may also be dragged across tissue 501, as depicted in FIGS. 5B and C. Dragging back side 207 across tissue 501 permits the ultrasound energy emanating from back side 207 to be directly delivered to tissue 501. It is important to note that ultrasound energy delivered to the tissue 501 by dragging the back side 207 of vibrating tip 105 across tissue 501 is mostly carried by radial waves released from tip 105. However, ultrasound energy carried by shear and longitudinal waves released from tip 105 may also reach tissue 501.

If tip 105 includes an orifice 215 extending from radial side 208 to back side 207, then dragging back side 207 across tissue 501, while tip 105 is ultrasonically vibrated, may simultaneously directly deliver ultrasound energy to tissue 501 and fragment unwanted tissue 502. Such a method of treating tissue 501 is depicted in FIG. 5C.

Furthermore, tip 105 may be rotated along the longitudinal axis 206 of horn 104 as back side 207 is dragged across tissue 501. Rotating a vibrating tip 105, while its back side 207 is dragged across tissue 501, permits ultrasonic energy carried by ultrasonic waves emanating from the various portions of back side 207 to be directly delivered to tissue 501. This may also occur when the angle of the ultrasound apparatus with respect to tissue 501 is increased and decreased.

FIGS. 6A-E depict different embodiments of an ultrasound tip 105 with a cavity connected to a horn 104. In all the embodiments depicted in FIGS. 6A-E the combination of horn 104 and ultrasound tip 105, with its radial sides forming a cavity, forms a shape similar to a spoon. The opening 210 of the cavity in the embodiment depicted in FIG. 6A is parallel to the longitudinal axis 206 of the ultrasound horn 104. This is the preferred embodiment. Alternatively, the opening 210 of the cavity, as depicted in FIGS. 6B to 6D, may be at an angle with respect to the axis 206 of the ultrasound horn 104. Other comparable shapes of combination of shapes, in addition to those depicted in FIGS. 6A-E, may be similarly effective as long as the opening 210 of the cavity is not oriented orthogonal to the axis 206 of horn 104.

FIGS. 6D & E also depict different possible embodiments of back surface 207 of ultrasound tip 105. As depicted in FIGS. 6D and 6E, back surface 207 may comprise a series of protrusions 601. The back surface 207 of the ultrasound tip 105 may be completely covered by such protrusions, as depicted in FIG. 6E. In the alternative, back surface 207 may contain an area including protrusions, as to create a jagged portion, and an area lacking protrusion, as to create smooth portion, as depicted in FIG. 6D.

FIG. 7 is an alternative embodiment of cavity 209 formed by the radial sides 208 of tip 105. In this embodiment a collection of radial sides 208 forms a polygonal-shaped paraboloid cavity 209. Alternative embodiments of an open cavity may be similarly effective in delivering ultrasound energy.

The ultrasound apparatus shown in FIG. 1 delivers ultrasound energy to a target area for the treatment of tissue, including the treatment of wounds and the removal of tumors. The tip is specially designed for controlled fragmentation and the simultaneous sonication of a target area via direct contact. The tip is also specially designed to focus ultrasound energy on a target area. The use of ultrasound may have multiple beneficial effects that include, but are not limited to, destroying bacteria, disinfecting a wound, stimulating cell growth, increasing blood flow, exerting less pressure on a wound, treating fistula and cavities, and removing unwanted tissue. These effects may aid in the healing process.

There are multiple methods that may be used to deliver ultrasound energy to a target area. Ultrasound energy may be delivered by contacting the target area with various portions of the ultrasound tip 105 such as the edge encircling cavity 209 or back surface 207. Ultrasound energy may also be delivered by contacting the target area with a coupling medium. The ultrasound energy is generally delivered from the radial side 208 of the ultrasound tip 105. Therefore, the ultrasound energy that is mainly delivered is radial waves. The use of radial waves, as compared to longitudinal waves, may allow the ultrasound tip 105 to vibrate horizontally on the target area rather than in a vertical motion.

The preferred coupling medium to use is a fluid, and the preferred fluid to use is saline. Other fluids such as drugs, antibiotics, antiseptics, etc may also be used. Both micro and macro cavitation may occur from the delivery of ultrasound energy through the coupling medium. Macro cavitation occurs in the coupling medium and results in sterilization of the target surface, fragmentation of tissue, and mechanical cleansing. Micro cavitation creates microstreaming inside the tissue, which is beneficial for tissue granulation. Fragmentation of unwanted tissue may result from the cavitation that occurs and the mechanical vibration of the ultrasound tip 105 on the tissue being treated.

The intensity of the ultrasound energy can be controlled through a variation in the parameters such as the frequency and amplitude at which the transducer induces the horn 104 and tip 105 to vibrate, as wells as the treatment time. The frequency at which the transducer induces the horn 104 and tip 105 to vibrate should be between 15 kHz to 20 MHz. The preferred low-frequency ultrasound range is 20 kHz-100 kHz. The more preferred low-frequency range is 25 kHz-50 kHz. The recommended low-frequency ultrasound is 30 kHz. The preferred high-frequency ultrasound range is 0.7 MHz-3 MHz. The recommended high-frequency ultrasound is 0.7 MHz. The amplitude of the low-frequency ultrasound vibrations induced within the horn 104 and tip 105 can be 5 microns or greater. The preferred low-frequency amplitude is in the range of 30 microns to 100 microns. The recommended low-frequency amplitude is 100 microns. The amplitude of the high-frequency ultrasound vibrations induced within the horn 104 and tip 105 can be 1 microns or greater. The preferred high-frequency amplitude is at least 5 microns. The recommended high-frequency amplitude is 10 microns.

There are a variety of factors that may influence treatment time. These factors may include the type of tissue being treated, the condition of a wound, the state of a wound, and the location of a wound.

Although specific embodiments and methods of use have been illustrated and described herein, it will be appreciated by those of ordinary skill in the art that any arrangement that is calculated to achieve the same purpose may substituted for the specific embodiments and methods shown. It is to be understood that the above description is intended to be illustrative and not restrictive. Combinations of the above embodiments and other embodiments as well as combinations of the above methods of use and other methods of use will be apparent to those having skill in the art upon review of the present disclosure. The scope of the present invention should be determined with reference to the appended claims, along with the full scope of equivalents to which such claims are entitled.

I claim:

1. An apparatus for the treatment of tissue with ultrasound energy by direct contact, comprising:
    a) an ultrasound horn containing:
        i. a proximal end including a proximal surface;
        ii. a distal end opposite the proximal end including a distal surface;
        iii. a radial surface extending between the distal end and the proximal end; and
        iv. a longitudinal axis extending through the horn from the proximal end to the distal end;
    b) an ultrasound tip connected to the distal end of the horn capable of delivering ultrasound energy to the tissue comprising:
        i. a back side;
        ii. a radial side opposite the backside forming a paraboloid cavity including an opening wherein a plane including the opening is not oriented orthogonal to the longitudinal axis of the horn; and
        iii. a jagged edge at least partially encircling the opening of the cavity;
    c) at least one channel running through at least a portion of the horn and into the cavity, containing an opening within a surface of the horn, and an opening within the radial side of the tip; and
    d) a non-atomized coupling medium delivered to the cavity through at least one of the channels opening within the radial side of the tip.

2. The apparatus according to claim 1, further comprising a transducer connected to the proximal end of the horn capable of inducing the horn and tip to vibrate at a frequency in the range of approximately 15 kHz-approximately 20 MHz.

3. The apparatus according to claim 1, further comprising a transducer connected to the proximal end of the horn capable of inducing vibrations within the horn and tip with an amplitude of at least 1 micron.

4. The apparatus according to claim 1, characterized by the combination of the ultrasound horn and the ultrasound tip forming a shape similar to a spoon.

5. The apparatus according to claim 1, further comprising a jagged surface on at least a portion of the back side of the tip.

6. The apparatus according to claim 1, further comprising a transducer connected to the proximal end of the horn driven by a frequency selected from the group consisting of continuous and pulsed.

7. The apparatus according to claim 1, further comprising a transducer connected to the proximal end of the horn driven by a frequency selected from the group consisting of fixed and modulated.

8. The apparatus according to claim 1, further comprising a transducer connected to the proximal end of the horn driven by a wave selected from the group consisting of sinusoidal, rectangular, trapezoidal and triangular wave form.

9. The apparatus according to claim 1, characterized by the paraboloid cavity having a focus lying outside of the cavity.

10. The apparatus according to claim 1, further comprising an orifice extending from the radial side of the tip to the back side of the tip.

11. The apparatus according to claim 1, further comprising a transducer connected to the proximal end of the horn capable of inducing vibrations within the horn and tip sufficient to induce cavitations within the coupling medium delivered to the tip.

\* \* \* \* \*